United States Patent
Tsao et al.

(10) Patent No.: US 6,930,766 B2
(45) Date of Patent: Aug. 16, 2005

(54) FIBER MEASUREMENT SYSTEM

(75) Inventors: Shyh-Lin Tsao, Taipei (TW);
Wen-Ming Cheng, Taoyuan (TW);
Pin-Chun Lin, Taoyuan (TW);
Chin-Jen Leu, Taoyuan (TW)

(73) Assignee: Walsin Lihwa Corp. (TW)

( * ) Notice: Subject to any disclaimer, the term of this patent is extended or adjusted under 35 U.S.C. 154(b) by 410 days.

(21) Appl. No.: 10/215,145

(22) Filed: Aug. 8, 2002

(65) Prior Publication Data

US 2003/0126892 A1 Jul. 10, 2003

(30) Foreign Application Priority Data

Jan. 8, 2002 (TW) .................................... 91100162 A

(51) Int. Cl.[7] .............................................. G01N 21/00
(52) U.S. Cl. ................................................. 356/73.1
(58) Field of Search ......................... 356/73.1; 65/144; 250/227.11, 227.14–227.19; 385/123–128

(56) References Cited

U.S. PATENT DOCUMENTS

| | | | |
|---|---|---|---|
| 4,081,258 A | | 3/1978 | Goell et al. |
| 4,902,327 A | | 2/1990 | Levinson |
| 5,245,400 A | * | 9/1993 | Anjan et al. ............... 356/73.1 |
| 5,262,639 A | | 11/1993 | Vokey et al. |
| 6,434,310 B1 | * | 8/2002 | Liu et al. ..................... 385/123 |
| 6,701,052 B2 | * | 3/2004 | Berkey et al. ............... 385/126 |
| 6,753,520 B2 | * | 6/2004 | Spirin et al. ............ 250/227.16 |

OTHER PUBLICATIONS

F. Wilczewski, Determination of the Field Radius w∞ from Bending Loss Measurements of Optical Fibers with Arbitrary Index Profile, IEEE Photonics Technology Letters, vol. 8, 1997, pp. 90–91.

M. Miyamoto et al., "Bending Loss Evaluation of Single–Mode Fibers with Arbitrary Core Index Profile by Far–Field Pattern", Journal of Lightwave Technology, vol. 8, 1990, pp. 673–677.

W. Freude et al., "Propagation Constant of Single–Mode Fibers Measured from the Mode–Field Radius and from the Bending Loss", Jornal of Lightwave Technology; vol. 7, pp. 225–228.

* cited by examiner

*Primary Examiner*—Tu T. Nguyen
(74) *Attorney, Agent, or Firm*—Volpe and Koenig, P.C.

(57) ABSTRACT

A fiber measurement system for obtaining a fiber bending loss data of a moving fiber when compared with a static fiber is provided. The system includes an optical transmitter for generating a first optical modulating signal, a first optical coupling device electrically connected to the optical transmitter for coupling the first optical modulating signal from the static fiber to the moving fiber, a perturbing device electrically connected to the first optical coupling device for modulating the first optical modulating signal of the moving fiber to a second optical modulating signal, a second optical coupling device electrically connected to the perturbing device for coupling the second optical modulating signal from the moving fiber to the static fiber, an optical receiver electrically connected to the second optical coupling device for reading the second optical modulating signal, and a filter electrically connected to the optical receiver for filtering the second optical modulating signal, thereby obtaining the fiber bending loss data.

14 Claims, 12 Drawing Sheets

FIBER MEASUREMENT SYSTEM

FIELD OF THE INVENTION

The present invention is related to a measurement system, and more particularly to an on-line dynamic fiber measurement system for measuring a bending loss data of a moving fiber.

BACKGROUND OF THE INVENTION

Some incorrect optical fiber/cable manufacturing processes or steps, such as various distributed materials of a Preform, an incorrect tension control during drawing out the fiber, a bending, a mechanical stress, an improper coloring and doubling process and a wrong UV value and jelly control, generate an excessive fiber loss resulting in the optical fiber quality without control. Therefore, a trouble with the optical fiber/cable manufacturing processes or steps is generated and the cost thereof will increase.

Although some measuring methods related to the fiber bending loss are disclosed, these measuring methods include complicated calculation procedures limited in an off-line measurement and are merely used during drawing out the optical fiber. Moreover, these measuring methods do not conform to the fiber to the home (FTTH), urgent demands for expanding short patch cord yield and keeping optical fiber quality from loss. Furthermore, if every section optical fiber loss is not measured automatically and is merely offline measured by using a sampling inspection, the inspection cost by using manpower would be wasted and the actual demand would be ignored.

Presently, several main practical techniques used for measuring the optical fiber/cable quality are as follows.

A method for measuring bending loss of an optical fiber with an arbitrary index to determine the field radius $\omega\infty$ is disclosed by F. Wilczewski, in "Determination of the Field Radius $\omega\infty$ from Bending Loss Measurement of Optical Fibers with Arbitrary Index Profile", IEEE Photonics Technology Letters, Volume 8, 1997, pages 90–91. Because the bending loss of the optical fiber is a function with a bending radius thereof, the field radius $\omega\infty$ could be acquired by applying this method. A valid bending radius of the optical fiber with the arbitrary index is similarly obtained by comparing between this method and a far-field method. This method is theoretically possible but includes complicated calculation procedures so that this method is merely understood and used by operating staffers skilled in the art.

A method of measuring a bending loss of a single mode fiber used for the range within an arbitrary fiber core index and based on a far-field measurement is disclosed by M. Miyamoto, T. Sakai, R. Yamauchi and K. Inada, in "Bending Loss Evaluation of Single-Mode Fibers with Arbitrary Core Index Profile by Far-Field Pattern", Journal of Lightwave Technology, Volume 8, 1990, pages 673–677. The precision is completely determined by measuring the far-field so that it is hard to popularize and not used for the practical application, particularly to the measurement with the quality of the optical fiber/cable and the bending loss thereof.

A propagation constant of single-mode fibers deduced by measuring a mode-field radius and a bending radius is disclosed by W. Freude, E. K. Sharma and A. Sharma, in "Propagation Constant of Single-Mode Fibers Measured From the Mode-Field Radius and From the Bending Loss", Journal of Lightwave Technology, Volume 7, 1989, pages 225–228. A near-field radius having a function relation with a wavelength is measured by using a valid value of a far-field, and then these data trend is simulated by using a minimum square method so that an experiential formula for calculating the propagation constant is acquired. And an integral constant of bending loss also is obtained. However, the method is too complicated to calculate.

A method of monitoring an optical fiber's attenuation during drawing out the optical fiber is disclosed by J. E. Goell et al., in "Method for Using On Line Optic Fiber Loss Monitor", U.S. Pat. No. 4,081,258, filed on Mar. 28, 1978. When the optical fiber is reeled off, light is transmitted and received by dual tip axial optical fiber take-up axis and pay-off axis and a central alignment trench. However, problems of the vibration and the offset could not be overcome during the process of reeling off the optical fiber. And, the optical fiber from the take-up axis and the pay-off axis to the central alignment trench whether bears with high speed working and does not affect the quality of the optical fiber. Moreover, the method is only used in the optical fiber's attenuation and a fiber bending loss is not considered. Therefore, this method includes more limiting factors to limit the use thereof and does not conform to requests of active and passive components of optical fiber communication in the mass production.

A method for continuously monitoring bending loss characteristics of optical fibers during drawing out optical fibers is disclosed by F. H. Levimson, in "Monitoring Fiber Bend Loss Characteristics During Manufacture", U.S. Pat. No. 4,902,327, filed on Feb. 20, 1990. During drawing out the optical fibers, different guiding wheels with different bending radiuses are manufactured to generate a qualified bending radius. Moreover, because light leakage is a reversible reaction, different guiding wheels are respectively implanted into light signals and detecting light sources in a bending area of the optical fiber and the method for continuously monitoring bending loss characteristics of optical fibers during drawing out optical fibers is accomplished through lens' assistance. This method still has drawbacks that the points of implanting and detecting light are limited in their sizes and the light collimating technique is hard to achieve. In addition, a bending loss generated from incorrect cladding or coating cannot be measured by this method after cladding and coating optical fibers.

A technique for monitoring characteristics such as bending loss, moisture and tangled damage in the optical fiber/cable is disclosed by D. E. Vokey et al, in "Fiber Optic Cable Monitoring Method and Apparatus Including Moisture Detection and Bending Loss Detection", U.S. Pat. No. 5,262,639, filed on Nov. 16, 1993. Two laser light sources including different wavelengths are used to simulate and monitor the bending losses of the optical fiber/cable so that the optical cable structure is measured. The position of fusing contact is achieved by applying an encoding technique similar to an optical time-domain reflectometer (OTDR). However, the optical time-domain reflectometer (OTDR) includes lower analytical degree or ability in measuring within 1 meter in the length of the optical fiber, and anti-scattering in dynamic fibers is different than in static fibers.

Presently, the study focus and aspect in the field of the optical fiber communication have turned from a wide area network (WAN) to a metropolitan area network (MAN). There are many concerned to a residential access fiber network (RAFN), but an ideal for the fiber to the home (FTTH) is not accomplished yet. The components design of the wavelength division multiplexing (WDM) system has turned into that of the coarse wavelength division multiplexing (CWDM) system. That means an optical fiber network of fiber to the home (FTTH) will come soon and the demand of short patch cord within 10 meter will be increased. The optical fibers will be installed in families of terminal users not familiar with the optical fiber characteristics. Therefore, the optical fiber providers should provide every section fiber characteristics information for users in order to ensure stabilization and security of the optical fiber characteristics when products leave the factory. Furthermore, it is very important key technique that incidence and information of every section fiber including bending loss data is effectively and automatically measured on line during manufacturing.

It is therefore tried by the applicant to deal with the above situations encountered in the prior art.

SUMMARY OF THE INVENTION

It is therefore an object of the present invention to provide an online dynamic fiber measurement system to measure moving fiber characteristics and data.

It is another object of the present invention to provide the fiber measurement system by applying a dynamic optical coupling technique to obtain signals of a moving fiber and further obtain a bending loss data of a moving fiber.

It is another object of the present invention to provide the fiber measurement system, in which the manufacturing efficiency and quality of the optical fiber/cable could be promoted.

According to an aspect of the present invention, there is provided a fiber measurement system for obtaining a fiber bending loss data of a moving fiber when compared with a static fiber. The fiber measurement system includes an optical transmitter for generating a first optical modulating signal, a first optical coupling device electrically connected to the optical transmitter for coupling the first optical modulating signal from the static fiber to the moving fiber, a perturbing device electrically connected to the first optical coupling device for modulating the first optical modulating signal of the moving fiber to a second optical modulating signal, a second optical coupling device electrically connected to the perturbing device for coupling the second optical modulating signal from the moving fiber to the static fiber, an optical receiver electrically connected to the second optical coupling device for reading the second optical modulating signal, and a filter electrically connected to the optical receiver for filtering the second optical modulating signal, thereby obtaining the fiber bending loss data.

Preferably, the fiber measurement system further includes a fiber pay-off guiding wheel.

Preferably, the fiber measurement system further includes a fiber take-up guiding wheel.

Preferably, the first optical coupling device and the second optical coupling device are free space optical coupling devices.

Preferably, each of the free space optical coupling devices includes a static ferrule adaptor, a ferrule adaptor connector and a dynamic ferrule adaptor.

Preferably, the ferrule adaptor connector is formed by ceramics.

Preferably, the static ferrule adaptor mounts the static fiber therein and collocates with the ferrule adaptor connector for transmitting an optical modulating signal of the static fiber and adjusting a longitudinal offset distance of the static fiber.

Preferably, the dynamic ferrule adaptor mounts the moving fiber therein and collocates with the ferrule adaptor connector for transmitting an optical modulating signal of the moving fiber and to adjust a longitudinal offset distance of the moving fiber.

Preferably, the ferrule adaptor connector mounts the static ferrule adaptor and the dynamic ferrule adaptor therein for coupling the static fiber and the moving fiber within a specific numerical aperture and decreasing a lateral offset distance of the static fiber and the moving fiber.

Preferably, the perturbing device is a fiber external spatial perturbing device

Preferably, the fiber external spatial perturbing device is formed by a plurality of guiding wheels being a ceramic Preferably, the filter is an active band-pass filter Preferably, the active band-pass filter is constituted by an operational amplifier, a plurality of resistor and a plurality of capacitor According to another aspect of the present invention, there is provided a fiber measurement system for obtaining a fiber bending loss data of a moving fiber when compared with a static fiber. The vending system includes a first optical coupling device for coupling a first optical modulating signal generated from the static fiber to the moving fiber, a perturbing device electrically connected to the first optical coupling device for modulating the first optical modulating signal of the moving fiber to a second optical modulating signal, and a second optical coupling device electrically connected to the perturbing device for coupling the second optical modulating signal generated from the moving fiber to the static fiber, thereby filtering the second optical modulating signal to obtain the fiber bending loss data.

The present invention may best be understood through the following descriptions with reference to the accompanying drawings, in which:

DETAILED DESCRIPTION OF THE PREFERRED EMBODIMENT

A fiber measurement system for obtaining a fiber bending loss data of a moving fiber according to the present invention will now be described more detailedly with reference to the following preferred embodiments and one skilled in the art can accomplish the present invention in accordance with the preferred embodiments. It is to be noted that the following descriptions of the preferred embodiments of the present invention are presented herein for the purpose of illustration and description only. It is not intended to be exhaustive or to be limited to the precise from disclosed.

Figure 1:
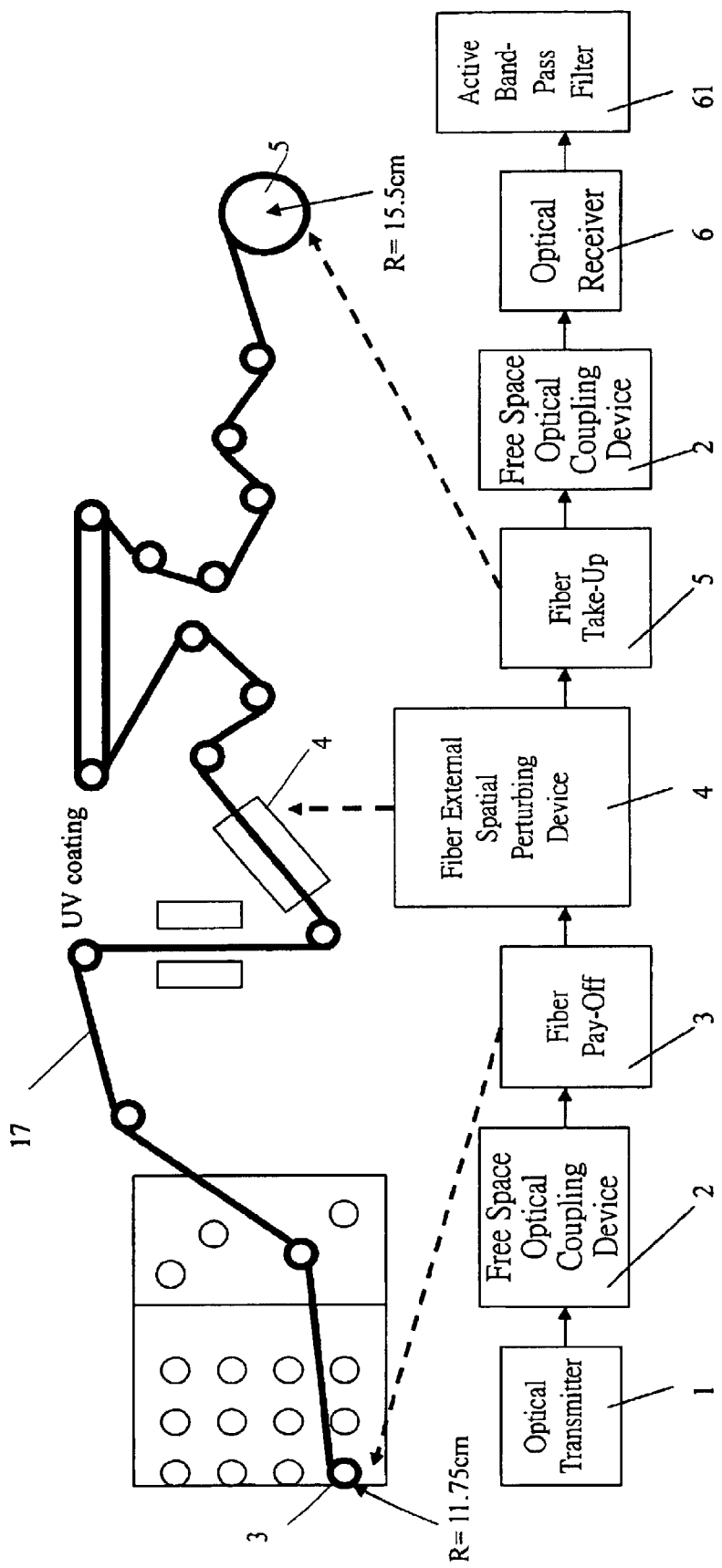
FIG. 1 is a schematic view showing a fiber measurement system on a ribbon fiber coating machine according to an embodiment of the present invention.

Please refer to FIG. 1, which is a schematic view showing a fiber measurement system on a ribbon fiber coating machine according to an embodiment of the present invention. The fiber measurement system includes an optical transmitter 1, a free space optical coupling device 2, a fiber pay-off guiding wheel 3, a fiber external spatial perturbing device 4, a fiber take-up guiding wheel 5, an optical receiver 6 and an active band-pass filter 61.

A first optical modulating signal (not shown) is generated from the optical transmitter 1 and is coupled from a static fiber (not shown) to a moving fiber (not shown) by the free space optical coupling device 2. Moreover, through the fiber external spatial perturbing device 4, the moving fiber generates a spatial deformation to generate a fiber bending loss, and the first optical modulating signal of the moving fiber is modulated by the fiber bending loss to be a second optical modulating signal (not shown). And, the second optical modulating signal is coupled from a moving fiber to a static fiber by the free space optical coupling device 2. The active band-pass filter 61 to generate a modulated signal filters the second optical modulating signal read by the optical receiver 6. Therefore, a fiber bending loss data in the present on-line fiber measurement system is obtained. Furthermore, the optical transmitter 1 and the optical receiver 6 apply a signal modulation technique to transmit an additional modulating signal, i.e. the first optical modulating signal, in the optical transmitter 1 to the present fiber measurement system, and a modulated signal, i.e. the second optical modulating signal, is returned in the optical receiver 6. Finally, a fiber bending loss signal is read out.

Furthermore, a moving fiber wrapping length signal with the fiber bending loss signal can be entered into a microprocessor. An attenuation of whole fiber is computed via a program and a bending loss characteristic of every section fiber is also obtained.

Through a computing method of the program, control parameters are adjusted by inputting a power signal form an optical transmitter, outputting the power signal from an optical receiver and controlling a movable three-dimensional (3D) fiber external spatial perturbing device shift platform so that fiber bending loss is obtained. Then, the bending loss characteristic of every section fiber is obtained through a computation of the moving fiber wrapping length signal. And, a warning of incorrect variables to generate an excess fiber bending loss is received in the fiber manufacturing process through computation of the program so as to maintain and ensure the quality of the fiber. The length of the bending loss characteristic of every section fiber is determined by an online fiber moving rate and a data access rate of the microprocessor.

Moreover, the warning of generating an excess fiber bending loss in different manufacturing processes and different manufacturers is generated through experimental data in the different manufacturing processes, i.e. a database is formed by adjusting variables of different manufacturers and variables of different manufacturing processes in the present on-line practical fiber measurement system, and a quality monitoring system in the fiber manufacturing process is formed through computation of the program and the present on-line practical fiber measurement system. The above-mentioned variables of different manufacturing processes could be an ultraviolet (UV), a tension and stress in optical fibers, a controllable fiber/Preform material, a fiber bending radius or effects of different wavelength. In addition, the quality monitoring system in the fiber manufacturing process feedback to a sub-system of the variables of different manufacturing processes through on-line practical measurement, and performs to adjust the variables via a closed circuit control system so as to improve and ensure unity and stability of the fiber quality.

Figure 2:
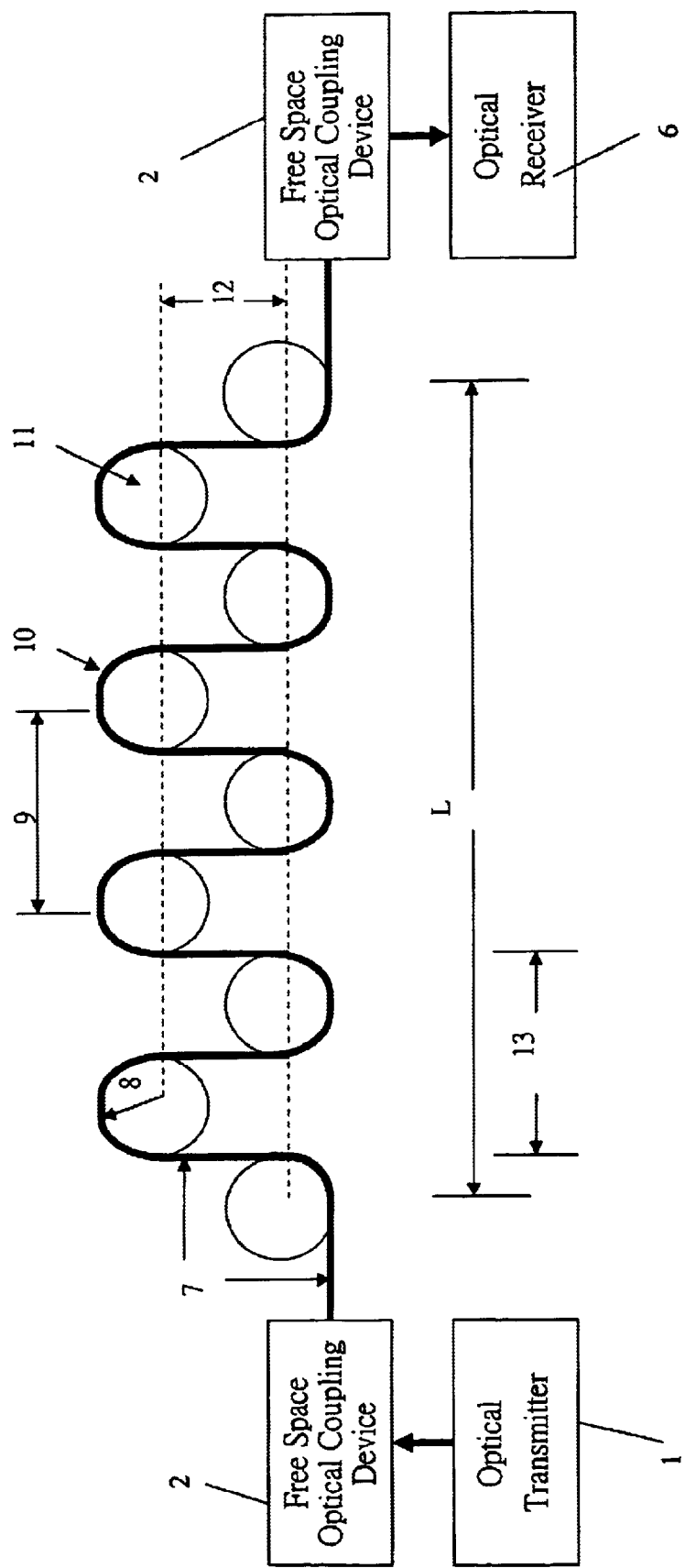
FIG. 2 is a schematic view showing a fiber external spatial perturbing device according to the embodiment of the present invention.
Figure 11:
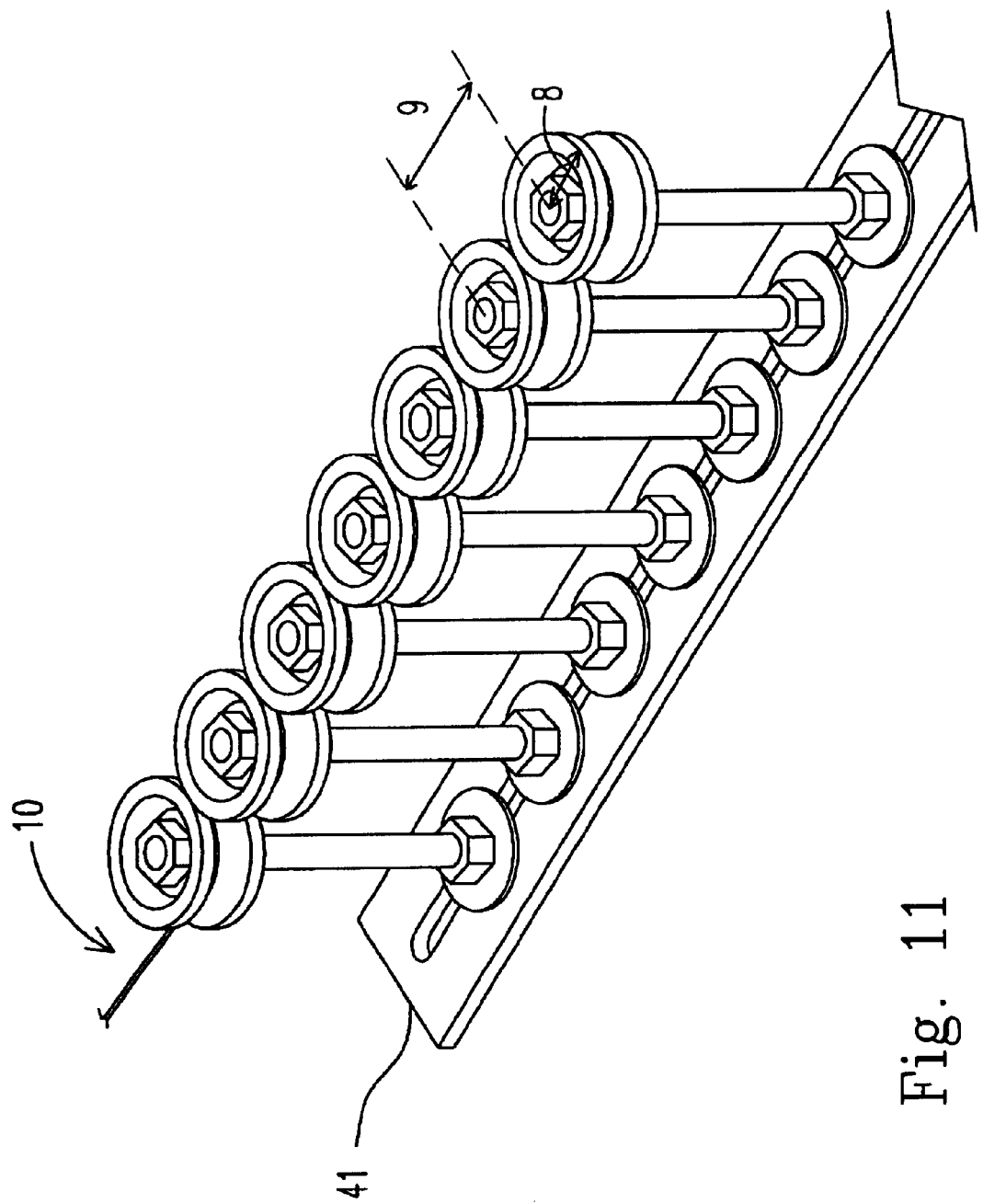
FIG. 11 is a schematic view showing a practical structure of the fiber external spatial perturbing device according to the embodiment of the present invention.

Please refer to FIG. 2, which is a schematic view showing a fiber external spatial perturbing device according to the embodiment of the present invention. The fiber external spatial perturbing device, as shown in FIG. 11, includes a moving bending fiber 10, ceramic guiding wheels 11 and a movable three-dimensional fiber external spatial perturbing device shift platform 41. Different control variables are generated from different sizes of the ceramic guiding wheels 11. The moving bending fiber 10 through the ceramic guiding wheel 11 is adjusted by the control variables to generate an expectable external spatial perturbation and a fiber bending loss is generated therewith. The movable three-dimensional fiber external spatial perturbing device shift platform 41 includes different control parameter such as a bending radius, a bending period, an deformation distance 12 of the moving bending fiber 10 and number of wrapping 11, wherein the bending radius is indicated that the size of the ceramic guiding wheel 11 is changeable and the bending period means a period 9 for perturbing the moving bending fiber 10 by the ceramic guiding wheel 11 is adjustable.

Figure 3A:
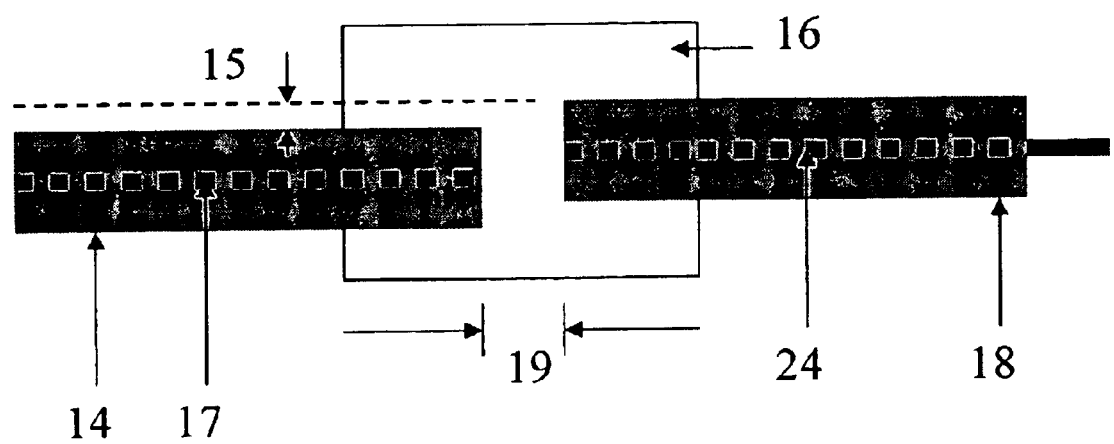
FIGS. 3A and 3B are respectively control parameters of a free space optical coupling device according to the embodiment of the present invention.
Figure 3B:
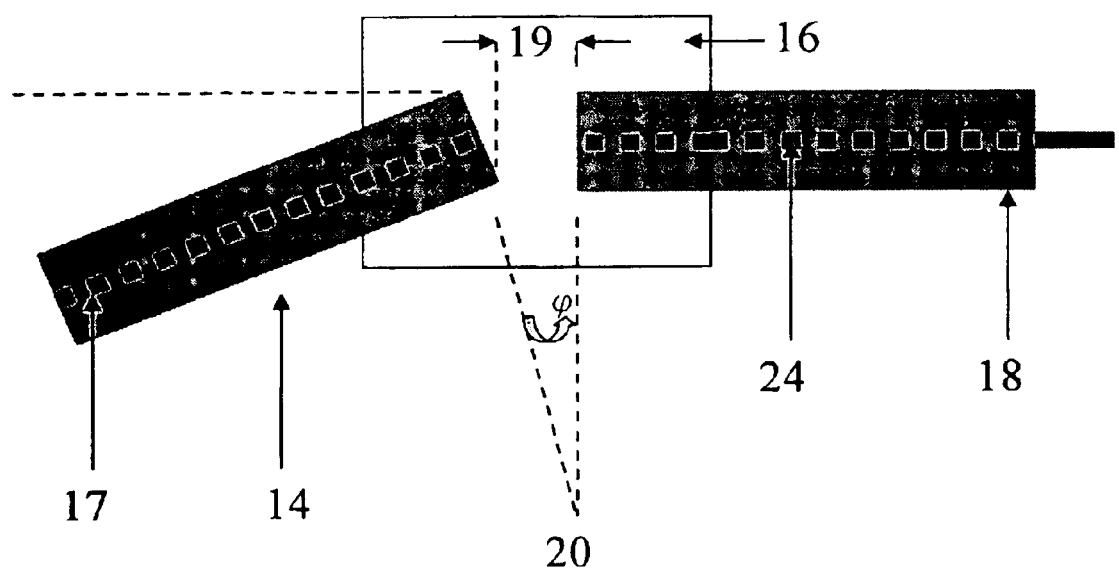

Please refer to FIGS. 3A and 3B, which are respectively control parameters of a free space optical coupling device according to the embodiment of the present invention. The free space optical coupling device includes a static ferrule adaptor 14, i.e. static fiber outer ceramic tube, a ferrule adaptor connector 16 and a dynamic ferrule adaptor 18, i.e. dynamic fiber outer ceramic tube. A signal in free space coupled from a static fiber 17 in the static ferrule adaptor 14 to a moving fiber 24 in the dynamic ferrule adaptor 18 is achieved by the free space optical coupling device. The controllable parameters include a fiber coupling lateral offset distance 15, a fiber coupling longitudinal offset distance 19 and a fiber coupling shift angle 20. The static ferrule adaptor 14 mounts the static fiber 17 therein and collocates with the ferrule adaptor connector 16 for transmitting an optical modulating signal of the static fiber 17 and adjusting a free space longitudinal offset distance of the static fiber 17. The dynamic ferrule adaptor 18 mounts the moving fiber 24 therein and collocates with the ferrule adaptor connector 16 for transmitting an optical modulating signal of the moving fiber 24 and to adjust a free space longitudinal offset distance of the moving fiber 24. The ferrule adaptor connector 16 mounts the static ferrule adaptor 14 and the dynamic ferrule adaptor 18 therein for coupling the static fiber 17 and the moving fiber 24 within a specific numerical aperture and decreasing a free space lateral offset distance of the static fiber 17 and the moving fiber 24.

Figure 4:
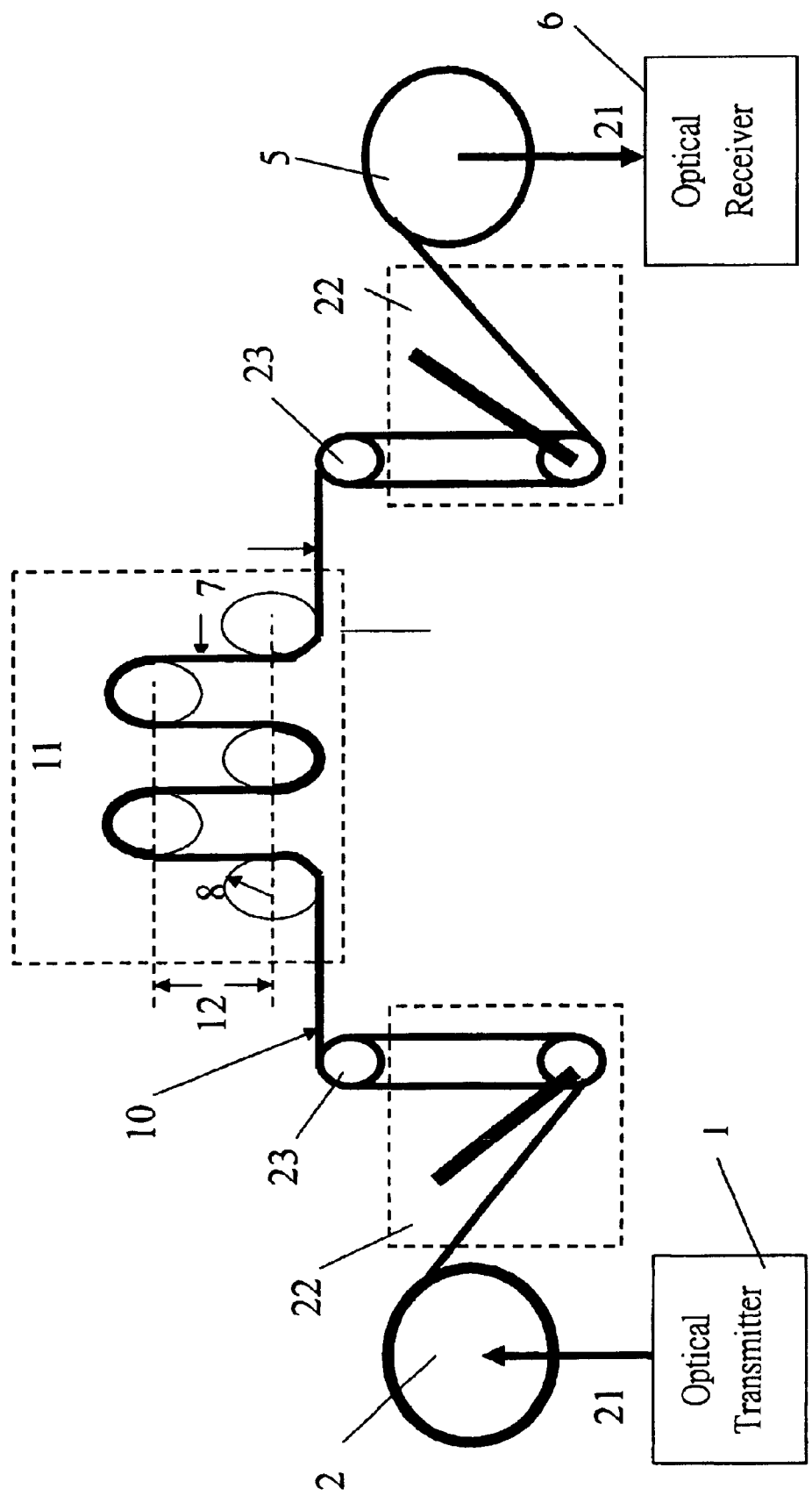
FIG. 4 is a schematic view showing an on-line fiber measurement system according to the embodiment of the present invention.

Please refer to FIG. 4, which is a schematic view showing an on-line fiber measurement system according to the embodiment of the present invention. A rate control system in the on-line equipment is a key factor influencing a dynamic testing efficiency except for FIGS. 2, 3A and 3B. And, the factor includes a movable proportion integration differentiation (PID) speed control device 22 and a static guiding wheel 23.

Figure 5:
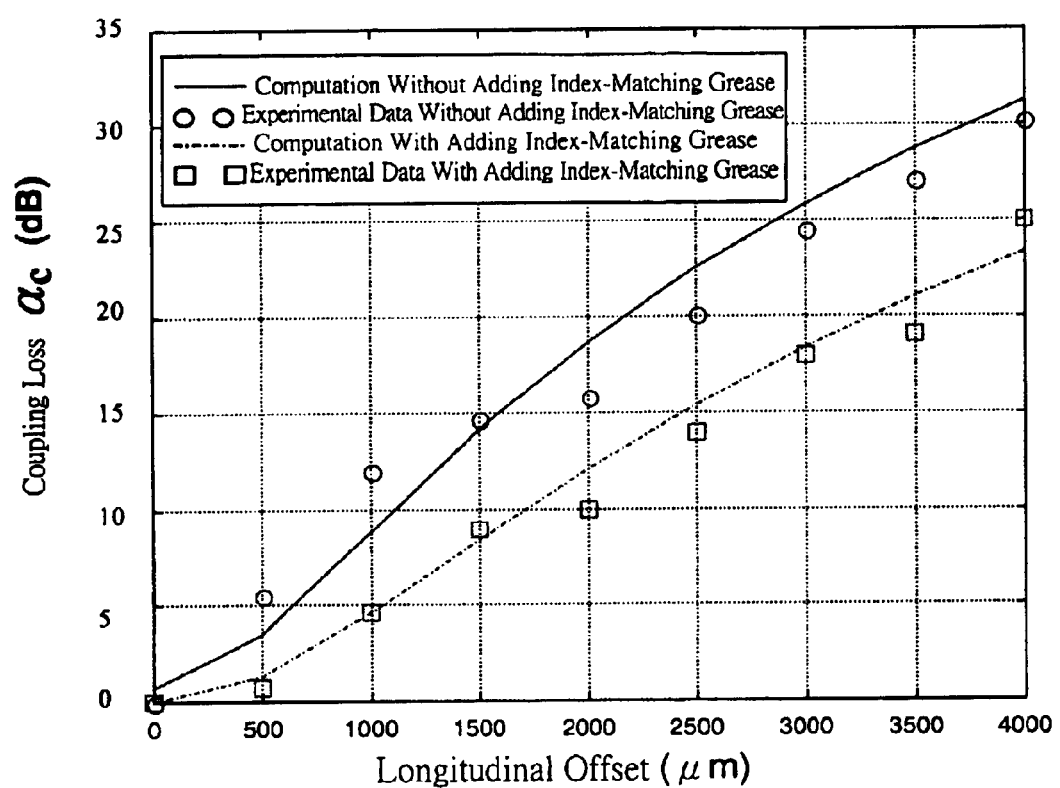
FIG. 5 is a plot showing a relative curve of comparison between the coupling loss and the longitudinal offset in the free space fiber coupling device according to the embodiment of the present invention.

Please refer to FIG. 5, which is a plot showing a relative curve of comparison between the coupling loss and the longitudinal offset in the free space fiber coupling device according to the embodiment of the present invention. The comparison plot between the coupling loss and the longitudinal offset is generated by adjusting the fiber coupling longitudinal offset distance 19 and decreasing effects of the fiber coupling lateral offset distance 15 and the fiber coupling offset angle 20 in the free space fiber coupling device 2. Furthermore, by adjusting different variable, e.g. adding an index-matching grease, on the basis of the fiber external spatial perturbing device shown in FIG. 2, a relative curve is generated.

Figure 6:
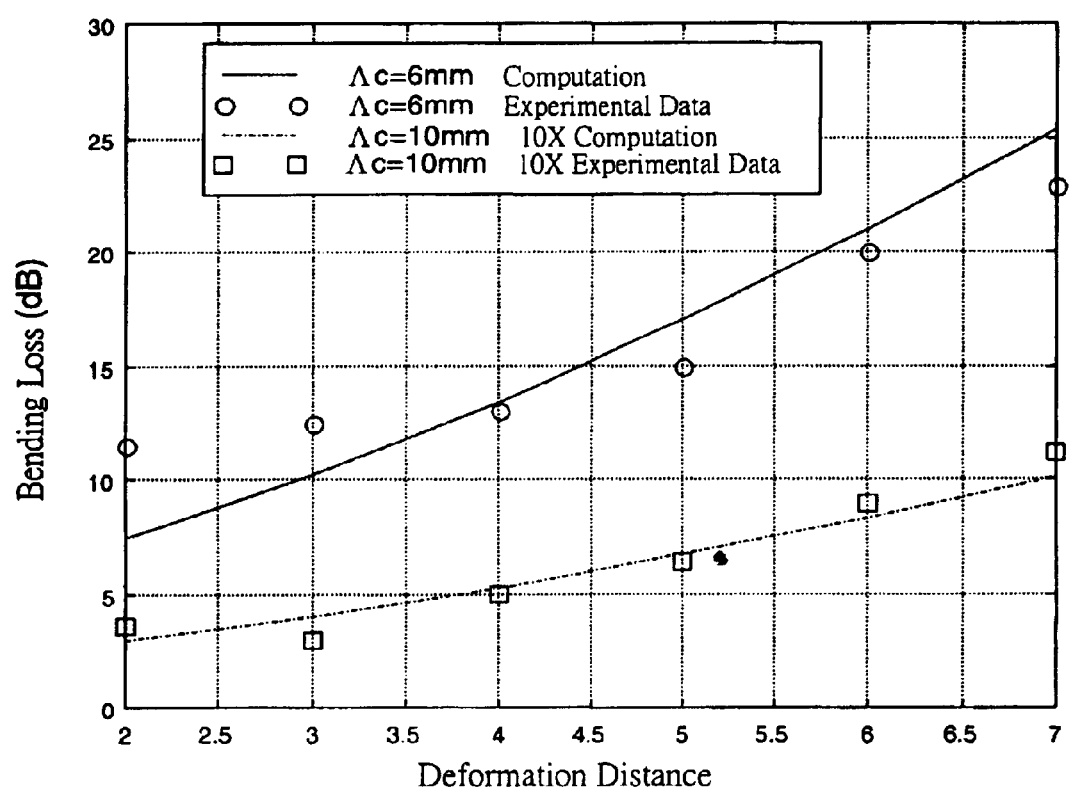
FIG. 6 is a plot showing a relative curve between the bending loss and the deformation distance when the wavelength is 1.31 $\mu$m and the winding number is 2 according to the embodiment of the present invention.
Figure 7:
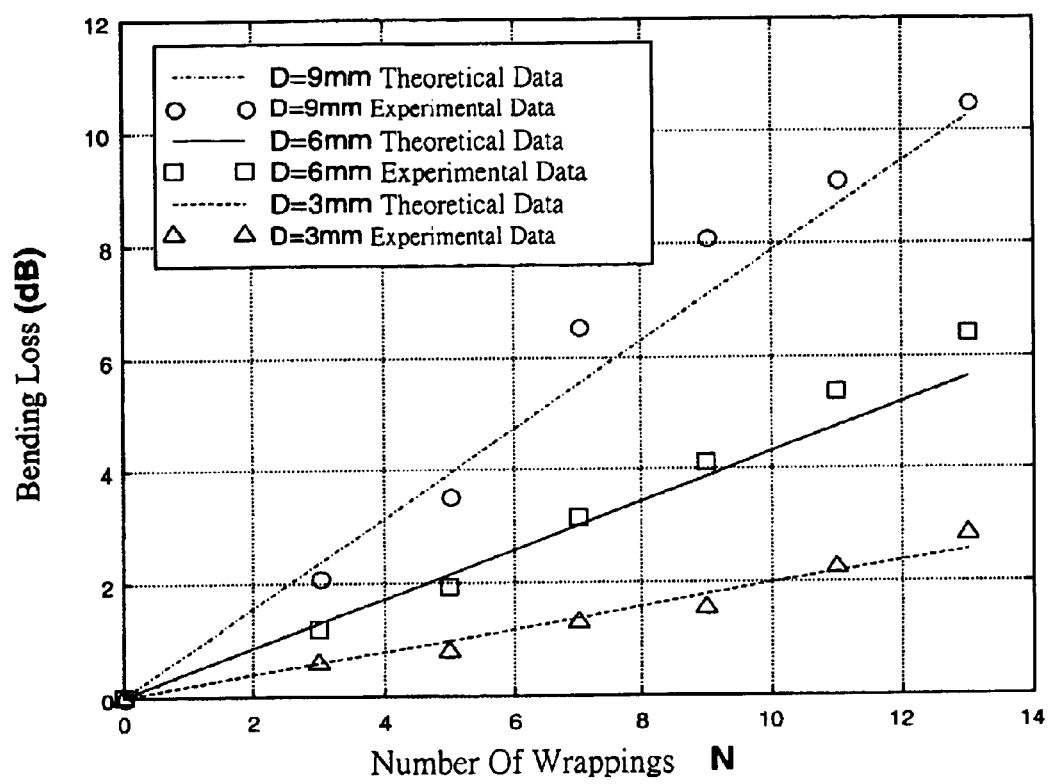
FIG. 7 is a plot showing a relative curve between the fiber bending loss and the number of guiding wheels according to the embodiment of the present invention.
Figure 8:
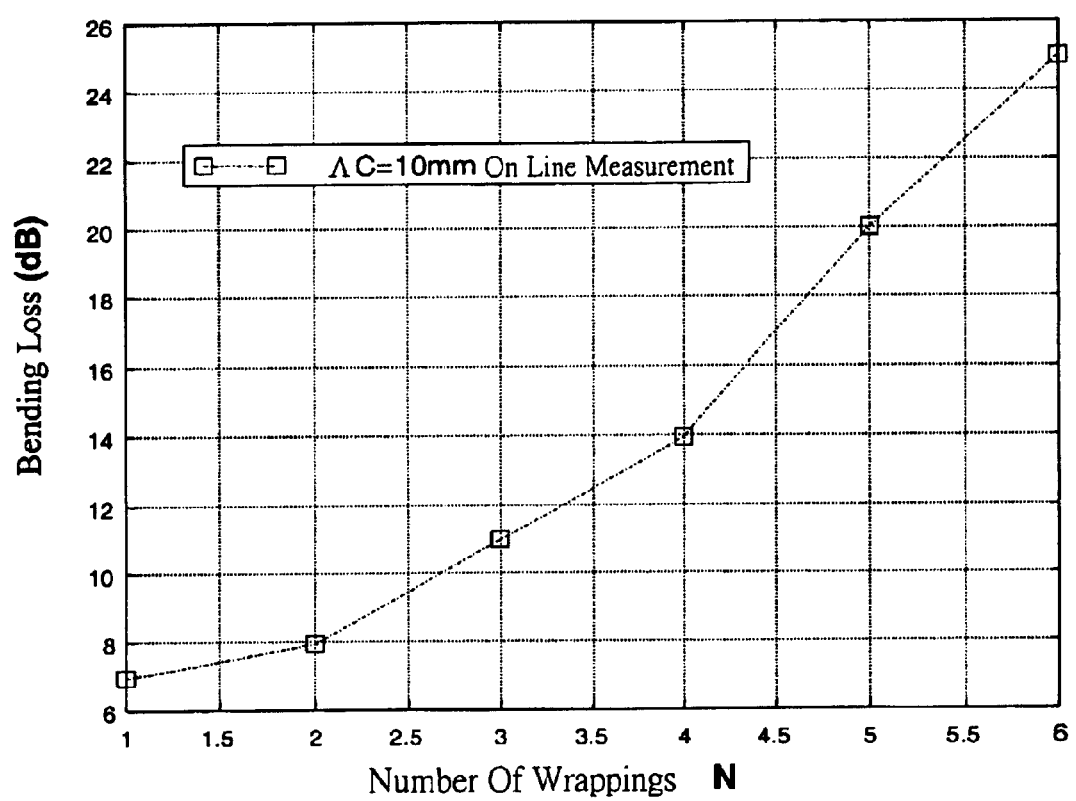
FIG. 8 is a plot showing a relative curve between the fiber bending loss and the number of guiding wheels in on-line measurement according to the embodiment of the present invention.
Figure 9:
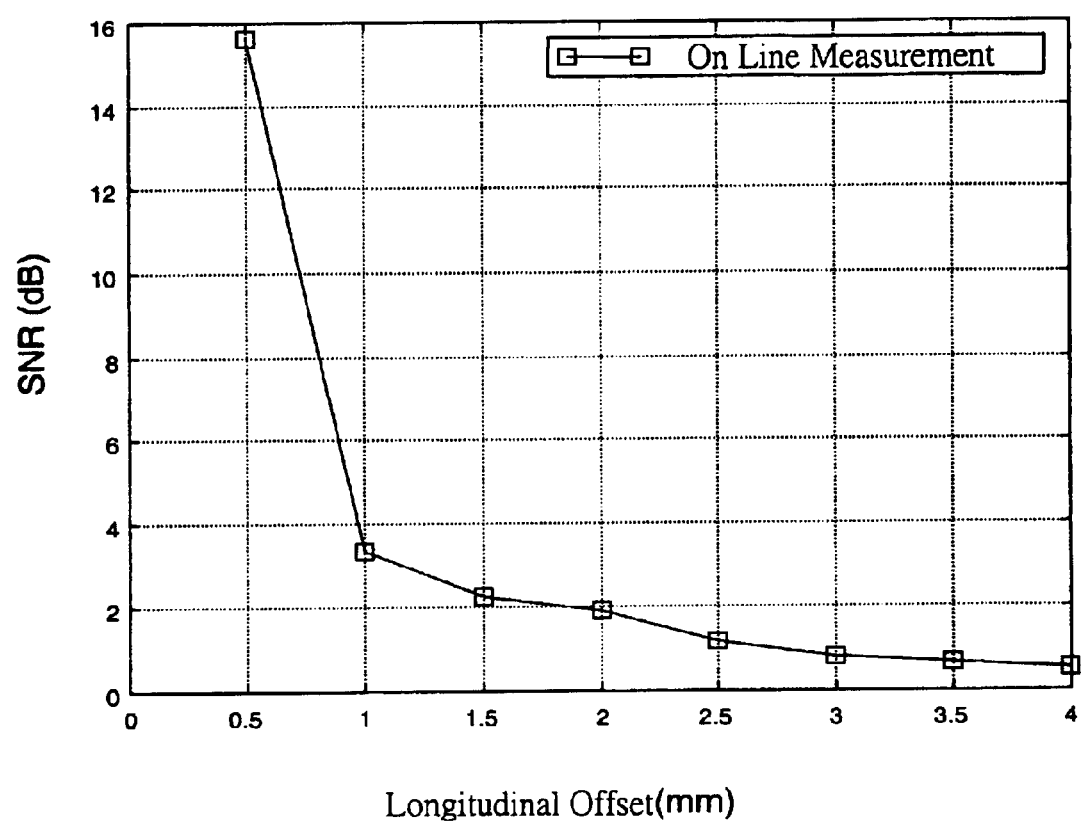
FIG. 9 is a plot showing a relative curve between the signal to noise ratio (SNR) in on-line measurement according to the embodiment of the present invention.

Please refer to FIG. 6, which is a plot showing a relative curve between the bending loss and the deformation distance when the wavelength is 1.31 $\mu$m and the winding number is 2 according to the embodiment of the present invention. FIG. 7 is a plot showing a relative curve between the fiber bending loss and the number of guiding wheels according to the embodiment of the present invention. FIG. 8 is a plot showing a relative curve between the fiber bending loss and the number of guiding wheels in on-line measurement according to the embodiment of the present invention. FIG. 9 is a plot showing a relative curve between the signal to noise ratio (SNR) in on-line measurement according to the embodiment of the present invention. FIG. 7 is a relative curve between theoretical data and experimental data by adjusting control parameters such as longitudinal optical coupling distance to generate a fiber bending loss in the free space optical coupling device shown in FIG. 3. And, FIG. 7 confirms variables for affecting the coupling loss to be merely limited in a longitudinal offset deviation according to the free space optical coupling device of FIG. 3. Moreover, FIG. 6 is a relative curve between theoretical data and experimental data when the wavelength is 1.31 $\mu$m and the winding number is 2 by using the fiber external spatial perturbing device shown in FIG. 2 to adjust control parameters in the on-line fiber measurement system of FIG. 4 to generate a fiber bending loss.

Figure 10:
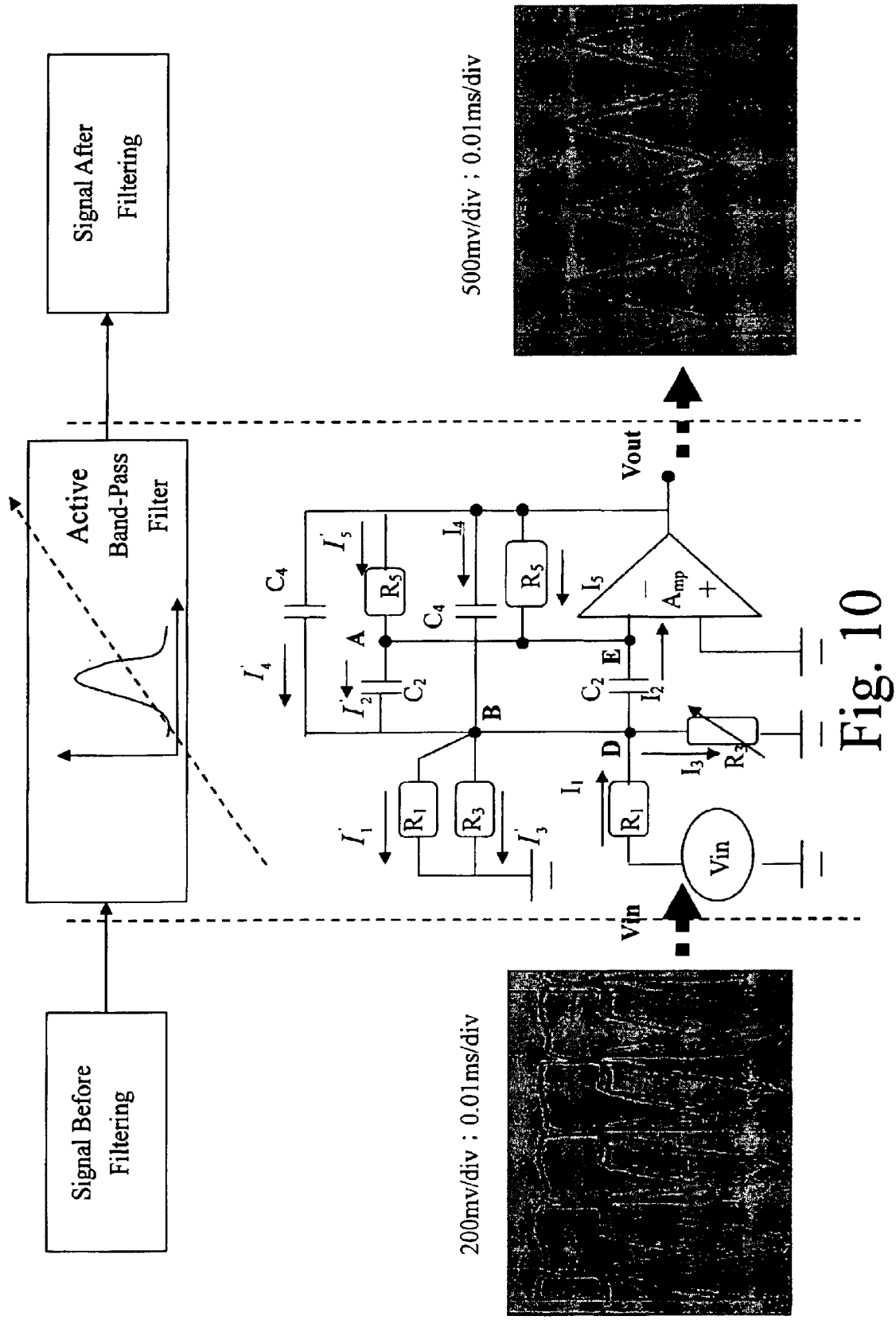
FIG. 10 is a schematic view showing a circuitry of an active band-pass filter according to the embodiment of the present invention.

Please refer to FIG. 10, which is a schematic view showing a circuitry of an active band-pass filter according to the embodiment of the present invention. The active band-pass filter includes an operational amplifier, a plurality of resistor $R_x$ and a plurality of capacitor $C_x$. And, a fiber bending loss data is obtained through an output signal after filtering.

Please refer to FIG. 11, which is a schematic view showing an practical structure of the fiber external spatial perturbing device according to the embodiment of the present invention. A moving fiber 10 is spatially perturbed to generate a mode conversion via the fiber external spatial perturbing device and generate a bending loss. And, adjustable variables include a bending radius, a bending period, a winding number and a bending angle.

In conclusion, drawbacks of the prior art would be overcome and the following distinguishing features are achieved according to the present invention.

An optical coupling barrier could be overcome by the present invention and an optical coupling operating technique is simplified. Moreover, the allowance of an optical coupling offset error is increased and a signal of the dynamic fiber is obtained by using a dynamic optical coupling technique. In short, a modulating signal is put in a laser light source by using a signal modulating technique to transmit with a laser light, and is inputted into a moving fiber to be read on an optical receiver. Furthermore, a signal to noise ratio (SNR) of the fiber measurement system is enhanced by applying an active band-pass filter and the modulating signal is return to obtain a fiber bending loss data.

The present invention includes a simple components assembly, has a lower cost and is easily operated. Moreover, the present invention could online monitor quality during manufacturing the optical fiber/cable. Therefore, the manufacturing efficiency and quality of the optical fiber/cable could be enhanced.

The present invention could be applied in production and testing system of active and passive components of the optical fiber/cable for promoting producing automatically and quality identically.

The optical fiber communication applying the wavelength division multiplexing (WDM) system has entered into the network of fiber to the home (FTTH), and the demand of short patch cords within 10 meter will be increased. The present invention could decrease the cost of manufacturing patch cords or fiber process and enhance the quality of the patch cords.

The present invention could provide a fiber bending loss wavelength response data because of on-line measuring a fiber bending loss. And, such data is an important information to network users in the wavelength division multiplexing (WDM) system of the optical fiber communication.

While the invention has been described in terms of what are presently considered to be the most practical and preferred embodiments, it is to be understood that the invention need not be limited to the disclosed embodiment. On the contrary, it is intended to cover various modifications and similar arrangements included within the spirit and scope of the appended claims that are to be accorded with the broadest interpretation so as to encompass all such modifications and similar structures. Therefore, the above description and illustration should not be taken as limiting the scope of the present invention which is defined by the appended claims.

What we claimed is:

1. A fiber measurement system for obtaining a fiber bending loss data of a moving fiber when compared with a static fiber, comprising:

an optical transmitter for generating a first optical modulating signal;

a first optical coupling device electrically connected to said optical transmitter for coupling said first optical modulating signal from said static fiber to said moving fiber;

a perturbing device electrically connected to said first optical coupling device for modulating said first optical modulating signal of said moving fiber to a second optical modulating signal;

a second optical coupling device electrically connected to said perturbing device for coupling said second optical modulating signal from said moving fiber to said static fiber;

an optical receiver electrically connected to said second optical coupling device for reading said second optical modulating signal; and a filter electrically connected to said optical receiver for filtering said second optical modulating signal, thereby obtaining said fiber bending loss data.

2. The fiber measurement system according to claim 1 further comprising a fiber pay-off wheel.

3. The fiber measurement system according to claim 1 further comprising a fiber take-up wheel.

4. The fiber measurement system according to claim 1 wherein said first optical coupling device and said second optical coupling device are free space optical coupling devices.

5. The fiber measurement system according to claim 4 wherein each of said free space optical coupling devices includes a static ferrule adaptor, a ferrule adaptor connector and a dynamic ferrule adaptor.

6. The fiber measurement system according to claim 5 wherein said ferrule adaptor connector is formed by ceramics.

7. The fiber measurement system according to claim 5 wherein said static ferrule adaptor mounts said static fiber therein and collocates with said ferrule adaptor connector for transmitting an optical modulating signal of said static fiber and adjusting a longitudinal offset distance of said static fiber.

8. The fiber measurement system according to claim 5 wherein said dynamic ferrule adaptor mounts said moving fiber therein and collocates with said ferrule adaptor connector for transmitting an optical modulating signal of said moving fiber and to adjust a longitudinal offset distance of said moving fiber.

9. The fiber measurement system according to claim 5 wherein said ferrule adaptor connector mounts said static ferrule adaptor and said dynamic ferrule adaptor therein for coupling said static fiber and said moving fiber within a specific numerical aperture and decreasing a lateral offset distance of said static fiber and said moving fiber.

10. The fiber measurement system according to claim 1 wherein said perturbing device is a fiber external spatial perturbing device.

11. The fiber measurement system according to claim 10 wherein said fiber external spatial perturbing device is formed by a plurality of guiding wheels being a ceramic.

12. The fiber measurement system according to claim 1 wherein said filter is an active band-pass filter.

13. The fiber measurement system according to claim 12 wherein said active band-pass filter is constituted by an operational amplifier, a plurality of resistor and a plurality of capacitor.

14. A fiber measurement system for obtaining a fiber bending loss data of a moving fiber when compared with a static fiber, comprising:

a first optical coupling device for coupling a first optical modulating signal generated from said static fiber to said moving fiber;

a perturbing device electrically connected to said first optical coupling device for modulating said first optical modulating signal of said moving fiber to a second optical modulating signal; and a second optical coupling device electrically connected to said perturbing device for coupling said second optical modulating signal generated from said moving fiber to said static fiber, thereby filtering said second optical modulating signal to obtain said fiber bending loss data.

* * * * *